(12) United States Patent
Ballard et al.

(10) Patent No.: US 7,329,690 B2
(45) Date of Patent: Feb. 12, 2008

(54) EFFECTIVENESS OF INVERTEBRATE PEST-CONTROL AGENTS

(75) Inventors: James B. Ballard, Medford, NJ (US);
John F. Wright, Cherry Hill, NJ (US);
James R. Collins, Glen Mills, PA (US);
Terry K. Porter, Valdosta, GA (US)

(73) Assignee: FMC Corporation, Philadelphia, PA (US)

( * ) Notice: Subject to any disclaimer, the term of this patent is extended or adjusted under 35 U.S.C. 154(b) by 482 days.

(21) Appl. No.: 10/497,215

(22) PCT Filed: Dec. 6, 2002

(86) PCT No.: PCT/US02/39224

§ 371 (c)(1),
(2), (4) Date: Nov. 19, 2004

(87) PCT Pub. No.: WO03/053345

PCT Pub. Date: Jul. 3, 2003

(65) Prior Publication Data

US 2005/0069567 A1    Mar. 31, 2005

Related U.S. Application Data

(60) Provisional application No. 60/339,651, filed on Dec. 12, 2001, now abandoned.

(51) Int. Cl.
| | |
|---|---|
| *A01N 53/12* | (2006.01) |
| *A01N 25/30* | (2006.01) |
| *A01N 25/00* | (2006.01) |
| *A01N 25/02* | (2006.01) |
| *A01N 25/04* | (2006.01) |
| *A01N 37/34* | (2006.01) |
| *A01N 53/14* | (2006.01) |

(52) U.S. Cl. ............. 514/531; 514/772; 424/DIG. 11

(58) Field of Classification Search ............... 514/521, 514/522, 531, 772, 772.1, 772.3, 784, 785, 514/788, 946, 964; 424/DIG. 11
See application file for complete search history.

(56) References Cited

U.S. PATENT DOCUMENTS 6,090,751 A * 7/2000 Chen .................. 514/66

FOREIGN PATENT DOCUMENTS

WO    WO 99/40784 A1    8/1999

OTHER PUBLICATIONS

Derian, P.J. et al., "Microemulsions of pyrethroids: phase diagrams and effectiveness of tristyrylphenol based surfactants," in: Devisetty, B.N. et al. Pesticide Formulations and Application Systems: $12^{th}$ Volume. American Society for Testing and Materials (Philadelphia). 1993, pp. 73-84.*
HCAPLUS abstract 1991:57487 (1991).*
HCAPLUS abstract 2000:52160 (2000).*
Database CAPLUS on STN, American Chemical Society (Columbus, OH, USA), accession No. 1991:673483, EP 432062 A, Concentrated pesticide microemulsions, which are stable when diluted (Rhone-Poulenc Chimie, FR.), Jun. 12, 1991, Fiard et al. abstract.

* cited by examiner

*Primary Examiner*—John Pak

(57) ABSTRACT

The present invention relates to the promotion of a continuous chemical barrier of a soil-born invertebrate pest control agent in soil in a locus where soil-borne invertebrate pests are suspected or known to exist. In particular the present invention relates to compositions of liquid soil-borne invertebrate pest control agents and selected adjuvants wherein the adjuvant improves the downward and lateral movement in the soil of the soil-born invertebrate pest control agent contained in the liquid soil-borne invertebrate pest control agent. The invention set forth herein finds particular utility with soil-born invertebrate pest control agents with a water solubility of 3 ppm, or less, such as bifenthrin.

11 Claims, No Drawings

EFFECTIVENESS OF INVERTEBRATE PEST-CONTROL AGENTS

This application is a 371 of PCT/US02/39224, filed on Dec. 6, 2002, which claims the benefit of U.S. Provisional Application 60/339,651, filed on Dec. 12, 2001 now abandoned.

The present invention relates generally to pesticidal compositions. In particular, it pertains to compositions of liquid invertebrate pest-control agents useful for control of soil-borne invertebrate pests.

BACKGROUND OF THE INVENTION

Soil-borne invertebrate pests, i.e., arthropods (crustaceans, arachnids, and insects) and nematodes, cause untold billions of dollars worth of damage throughout the world to crops, dwellings, and structures useful to humankind. Soil-borne insects attack the seeds and seedlings of most crops. For example, black cutworm (*Agrotis ipsilon*-Hufnagel) commonly feeds on seedlings of, for example, corn, at ground level, cutting off the stem and sometimes dragging the plants into their burrows. Most of the plant is not consumed but merely eaten enough to cause it to topple. Since the larvae occur burrowed near the roots of the host, it sometimes feeds on roots and the below-ground stem. Because of the nature of their feeding on young plants, this pest can do great damage in newly planted fields. Corn plants that are too large for larvae to cut through may have a hole bored into the stem. Large populations can decimate an entire field of corn seedlings. Yield losses to uncontrolled black cutworm can be as high as 25%.

Nematodes are among the most destructive plant-parasitic soil-borne organisms on a wide range of plants. For example, sting nematodes (*Beloizolainus longigicaudatus*) are ectoparasites of plant roots, where they remain in the soil and feed by inserting a long stylet or mouth spear into root tips. The nematodes then inject enzymes into root tissues and suck plant juices out through the stylet. Root tips typically cease growing in response to feeding by sting nematodes. Sting nematodes cause particular damage to young plants with a developing root system. Sting nematodes cause yield losses in many crops and can cause complete crop destruction with severe infestations. Damaged crops include vegetables (carrot, corn, crucifers, beans, potato, etc.), fruits (citrus, strawberry, etc.), agronomic crops (cotton, peanut, sorghum, soybean, etc.), turfgrasses (Bahiagrass, Bermudagrass, St. Augustinegrass, zoysiagrass, etc.) and forest crops (pine trees).

Termites, however, are undisputedly the most destructive of all soil-borne invertebrate pests. Termites are estimated to cause 1.5 billion dollars of damage to wooden structures and dwellings annually, and that an additional one billion dollars is spent on treatment. Depending on the type of termite, a colony can cover as much as 22,000 square feet. These industrious insects work 24 hours a day, gradually eating wood and any other cellulose containing material in their environment. Since they remain hidden within the wood in which they are feeding, in mud tubes, or in the soil, they typically wreak havoc undetected. There are two types of termites, described as i) dry wood termites, and ii) subterranean termites. Of these two types, the subterranean termites usually live in the soil (i.e., soil-borne), from which they build mud tubes to structural wood where they then feed.

Control of soil-borne invertebrate pests can be accomplished by strategic application of at least one invertebrate pest-control agent to the soil in a locus where there is an invertebrate pest infestation. When the invertebrate pest is termites, a standard method for placing the termiticide in the soil is by physical means. Such physical means include, inter alia, (1) the digging of trenches around the outside of a structure, then flooding the trenches with termiticide, or (2) by injecting the termiticide directly into the soil using a mechanical device, such as a soil rod. These methods are very labor-intensive, and require an inordinate amount of termiticide to be effective. Another method for control of soil-borne termites is by the application of a termiticide directly to the surface of soil, thereby in theory creating a chemical barrier in the soil when the termiticide leaches into the soil.

Invertebrate pest control agents having utility in application directly to the surface of soil are in the form of liquid invertebrate pest control agents. A liquid invertebrate pest control agent is defined as a composition comprised of a formulation containing an invertebrate pest control agent where the formulation is dispensed in an aqueous medium prior to its application to a locus where invertebrate pest control is needed. For example, a liquid termiticide is therefore defined as a composition comprised of a formulation containing a termiticide where the formulation is dispensed in an aqueous medium prior to its application to a locus where termite control is needed.

Examples of formulations that can be dispensed in aqueous medium to provide a liquid invertebrate pest control agent include, without limitation, formulations of bifenthrin, sold by FMC Corporation under the names and trademarks of TALSTAR® GC FLOWABLE INSECTICIDE/MITICIDE, or TALSTAR® TERMITICIDE/INSECTICIDE. However, the invertebrate pest control agent in most liquid invertebrate pest control agents prepared from these formulations are not particularly mobile in the soil. That is to say, the invertebrate pest control agent does not appreciably spread downwardly and laterally from its point of application on the surface of the soil. Reasons for the immobility of such invertebrate pest control agents when placed on the soil include, inter alia, (1) the limited water solubility of the invertebrate pest control agent, for example, of about 3 parts per million (ppm) or less, and (2) the tendency of the invertebrate pest control agent to bind to the soil. Consequently when a liquid invertebrate pest control agent containing such relatively water-insoluble, soil-binding invertebrate pest control agents are applied to the soil, there may be gaps, or thinly treated areas, in the desired continuous chemical barrier caused by the immobility of the invertebrate pest control agent in the soil. Soil-borne insects such as termites, therefore, can gain access to food sources/structures through gaps and thinly treated areas in the chemical barrier. To aid in providing the continuous chemical barrier in the soil, a method and/or compositions of liquid invertebrate pest control agents that promote increased downward and lateral movement of relatively water-insoluble, soil-binding invertebrate pest control agents is clearly needed.

SUMMARY OF THE INVENTION

The objects of the present invention therefore include 1) promotion of a continuous chemical barrier to prevent access of soil-borne invertebrate pests to their food sources by use of novel compositions of liquid invertebrate pest control agents and at least one adjuvant, in which the adjuvant promotes an increase in downward and lateral movement in the soil of the invertebrate pest control agent that is contained in the liquid invertebrate pest control agent, and 2) a method of controlling soil-borne invertebrate pests using the novel compositions.

Accordingly, one aspect of the present invention are compositions containing a liquid invertebrate pest control agent, and at least one adjuvant, where the liquid invertebrate pest control agent further includes at least one invertebrate pest control agent having a water solubility of about 3 ppm or less in which the adjuvant promotes at least a 20% increase in the downward and lateral movement of the invertebrate pest control agent in soil. Other aspects of the present invention will also be apparent.

DETAILED DESCRIPTION OF THE INVENTION

It has now been unexpectedly found that when at least one of a select number of adjuvants is added to a liquid invertebrate pest control agent, the downward and lateral movement in the soil of the invertebrate pest control agent contained therein is increased. The addition of at least one adjuvant to a liquid invertebrate pest control agent provides novel compositions that aid in promoting a continuous chemical barrier to invertebrate pests in the soil around a crop, or around a structure or dwelling. Specifically, the novel compositions are those containing a liquid soil-borne pest control agent and at least one adjuvant, where the liquid soil-borne pest control agent further includes at least one soil-borne pest control agent having a water solubility of about 3 ppm, or less, in which the adjuvant promotes at least a 20% increase in downward and lateral movement of the soil-borne invertebrate pest control agent in soil. Preferably, the adjuvant promotes at least a 30% increase in downward and lateral of the soil-borne invertebrate pest control agent.

As set forth above, a liquid soil-borne invertebrate pest control agent is comprised of any formulation containing an invertebrate pest control agent where the formulation is dispensed in an aqueous medium prior to its application to a locus where soil-borne invertebrate pest control is needed. That is to say, a liquid invertebrate pest control agent is comprised of 1) a formulation of an invertebrate pest control agent, and 2) an aqueous medium. There may be more than one formulation for a particular invertebrate pest control agent, depending upon how that invertebrate pest control agent is to be used to control soil-borne invertebrate pests. The compositions of the present invention are preferably derived from commercially available formulations of invertebrate pest control agents, although they do not necessarily need to be derived from such formulations. All formulations of invertebrate pest control agents that are dispensed in an aqueous medium prior to application are, therefore, within the scope of the present invention. Preferred are those formulations of invertebrate pest control agents in which the invertebrate pest control agent contained therein is relatively insoluble in water, i.e., has solubility in water of 3 ppm, or less. Without limitation, a few of these formulations and the active invertebrate pest control agent contained therein are set forth below:

| Examples of Formulations From Which a Liquid Invertebrate Pest Control Agent May be Derived by Dispensing the Formulation in an Aqueous Medium | Invertebrate Pest Control Agent In Formulation | Manufactured By: |
|---|---|---|
| TRIBUTE ® Termiticide/Insecticide Concentrate | Fenvalerate | AgrEvo Environmental Health, Inc. |
| TALSTAR ® TERMITICIDE/INSECTICIDE | Bifenthrin | FMC Corporation |
| TALSTAR ® GC FLOWABLE INSECTICIDE/ MITICIDE | Bifenthrin | FMC Corporation |
| DRAGNET ® FT TERMITICIDE/INSECTICIDE | Permethrin | FMC Corporation |
| PREVAIL ® FT TERMITICIDE | Cypermethrin | FMC Corporation |
| PHANTOM ® Termiticide/Insecticide | Chlorfenapyr | American Cyanamid |
| TERMIDOR ® SC Termiticide | Fipronil | Aventis Enviornmental Science |
| DURSBAN ® TC Termiticide | Chlorpyrifos | Dow AgroSciences |
| DELTAGARD ® TC Termiticide | Deltamethrin | AgrEvo Environmental Health, Inc. |
| BAYTHROID ® 2 Emulsifiable Pyrethroid Insecticide | Cyfluthrin | Bayer Corporation |
| KARATE ® with ZEON TECHNOLOGY ™ | Lambda Cyhalothrin | Syngenta Crop Protection, Inc. |
| FORCE ® INSECTICIDE | Tefluthrin | Syngenta Crop Protection, Inc. |

Those invertebrate pest control agents having a water solubility of about 3 ppm, or less that find utility in the present invention are fenvalerate, bifenthrin, permethrin, cypermethrin, chlorfenapyr, fipronil, chlorpyrifos, deltamethrin, cyfluthrin, lambda cyhalothrin, gamma cyhalothrin, tefluthrin, and their isomers, which includes optical enantiomorphs, diastereomers, and polymorphs, and mixtures thereof. Preferred invertebrate pest control agents in the context of the present invention are bifenthrin, permethrin, fenvalerate, cypermethrin, deltamethrin, their isomers, and mixtures thereof, and particularly preferred is bifenthrin.

As set forth above, the preferred soil-borne invertebrate pest control agents are members of the pyrethroid class of chemical compounds useful as, for example, insecticides/termiticides. It is expected that the soil mobility of all pyrethroids would be improved by invertebrate pest control compositions, and applications thereof, according to the present invention. Such pyrethroid compounds, in addition to those set forth above, include, without limitation, acrinathrin, allethrin, bioallethrin, barthrin, bioethanomethrin, cyclethrin, cycloprothrin, cyhalothrin, cyphenotrin, deltamethrin, dimethrin, empenthrin, fenfluthrin, fenpirithrin, fenpropathrin, fenvalerate, flucythrinate, fluvalinate, furethrin, imiprothrin, phenothrin, prallethrin, pyresmethrin, resmethrin, terallethrin, tetramethrin, tralomethrin, transfluthrin, transfluthrin, etofenprox, flufenprox, halfenprox, protrifenbute, silafluofen, and their isomers, which includes optical enantiomorphs, diastereomers, and polymorphs.

It is also expected that the soil mobility of invertebrate pest control agents with a water solubility higher than 3 ppm would also be improved by applications according to the present invention. For, example, one such invertebrate pest control agent is imidacloprid (water solubility 610 ppm), sold under the name and trademark of PREMISE® 75 INSECTICIDE in water-soluble bags, by Bayer Corporation.

It is also expected that the novel compositions of invertebrate pest control agents of the present invention would have utility for the protection of a host of commodities useful to humankind, albeit crops, structures, or dwellings, against a variety of soil-borne invertebrate pests. In addition to protection of structures or dwellings against, for example, termites, crops finding protection from soil-borne invertebrate pests by the use of the novel compositions of the present invention include, without limitation, root and tuber crops, such as potato, carrots, sweet potato, beets, and turnip to name a few; corn, beans, broccoli, cabbage, spinach, sugarcane, tomato, and trees, as well as many other crops.

Soil-borne invertebrate pests controlled by the novel compositions of the present invention include, without limitation, termites, nematodes, pillbugs, millipedes, centipedes, earwigs, seed corn maggot, corn rootworms, such as southern corn rootworm, western corn rootworm, Mexican corn rootworm, and spotted corn rootworm; white grubs, wireworms, corn root aphids, cutworms, such as black cutworm, granulate cutworm, and varigated cutworm; june beetles, chafers, hunting billbugs, lesser cornstalk borer, mole crickets, such as tawny mole cricket and southern mole cricket; white-fringed beetle, seed corn beetles; ants, such as thief ants, and cornfield ants; corn root aphids, sod webworm, as well as other soil-borne invertebrate pests. Preferably, the novel compositions of the present invention are useful in a locus encompassing i) structures and dwellings where protection from termites is desired and ii) crops, such as corn, and root and tuber crops, where protection from corn rootworms; and wireworms and nematodes, respectively, is desired.

As set forth above, when at least one of a selected number of adjuvants were added to a liquid invertebrate pest control agent prior to its application to soil, the downward and lateral movement in the soil of the invertebrate pest control agent contained therein was unexpectedly increased following application of the liquid invertebrate pest control agent to the soil. Adjuvants finding utility in promoting movement of an invertebrate pest control agent in the soil include, without limitation, the following:

(i) An emulsifier of 99% 2,4,6-tris[1-(phenyl)ethyl]phenyl-omega-hydroxy-poly(oxyethylene)sulphate—sold under the name and trademark of Soprophor™ 4D-384 by Rhone-Poulenc, Inc., Prospect Plains Road, Cranbury, N.J. 08512 USA;

(ii) A nonionic surfactant of 100% perfluoroalkylethanol—sold under the name and trademark of Fluowet OTN by Clariant, 2724 Springfount Trail, Lawrenceville, Ga. 30043;

(iii) A spray tank adjuvant blend of 83% highly refined paraffin-based petroleum oil and 17% alkyl and alkylarylpolyoxyethylene glycols—sold under the name and trademark of Drexel Activate Oil by Drexel Chemical Company, PO Box 9306. Memphis, Tenn. 38109-0306;

(iv) A nonionic surfactant of modified polysiloxane polyether—sold under the name and trademark of Break Thru S240 by Goldschmidt Chemical Corp., PO Box 1299, 914 East Randolph Road, Hopewell, Va. 23860;

(v) A non-ionic surfactant blend of alkyloxypolyethyleneoxyethanols of the formula $CH_3CH[(CH_2)_nCH_3][O(C_2H_4O)_mH]$ where n is 9-15, and m is 3-40—sold under the name and trademark of SM-9 by Safe Materials, Inc, Valdosta, Ga.;

(vi) A silicone surfactant 100% blend of 2-(3-hydroxypropyl)heptamethyltrisiloxane, ethoxylated acetate, allyloxypolyethylene glycol monallyl acetate, and polyethylene glycol diacetate—sold under the name and trademark of Sylgard® 309 by Wilber-Ellis Company, PO Box 16458, Fresno, Calif. 93755;

(vii) A biodegradable, low-foaming, non-ionic surfactant and penetrant containing primary alkyl polyoxyethylene ether and free fatty acids and adjuvants—sold under the name and trademark of Activator 90 by Loveland Industries, Inc., PO Box 1289, Greeley, Colo. 80632.

(viii) A nonionic surfactant blend of soybean based fatty acid and alcohol ethoxylates—sold under the name and trademark of Preference NIS by Cenex/Land O'Lakes Agronomy Company of St. Paul, Minn.;

(ix) An anionic surfactant blend of 58% ammonium linear alcohol ether sulfate—sold under the name and trademark of Rhodapex® CD-128 by Rhone-Poulenc, Inc., Prospect Plains Road, Cranbury, N.J. 08512 USA;

(x) An anionic surfactant blend of 58% ammonium nonylphenol ether sulfate—sold under the name and trademark of Rhodapex® CO-436 by Rhone-Poulenc, Inc., Prospect Plains Road, Cranbury, N.J. 08512 USA;

(xi) A blend of polyalkyleneoxide, modified polydimethylsiloxane, and nonionic surfactants—sold under the name and trademark of Thoroughbred by Estes Incorporated, Wichita Falls, Tex. 76303;

(xii) A nonionic detergent of 100% polyoxyethylene(10) isooctylcyclohexyl ether—sold under the name and trademark of Triton® X-100 by Aldrich Chemical Company, Inc., 1001 West Saint Paul Ave., Milwaukee, Wis. 53233; and mixtures thereof.

[Hereinafter Designated by Roman Numerals (i)-(xii)]

Preferred adjuvants selected from the above are (i), (ii), (iv), (v), (vi), (x), (xi), (xii), and mixtures thereof. More preferred adjuvants in the context of the present invention are (i), (ii), (xi), and mixtures thereof; and most preferred is adjuvant (i).

The compositions of the present invention were preferably derived from commercially available formulations of invertebrate pest control agents. For example, bifenthrin, sold by FMC Corporation under the names and trademarks of TALSTAR® GC FLOWABLE INSECTICIDE/MITICIDE, or TALSTAR® TERMITICIDE/INSECTICIDE, to name a few, find utility in the present invention. For example, using methods known to one skilled in the art, the formulation of invertebrate pest control agent was dispersed in an aqueous medium to provide a composition containing a pesticidally effective amount of the invertebrate pest control agent. To promote movement of the invertebrate pest control agent, such as bifenthrin, in the soil, an amount of adjuvant in the range of about 0.001% to about 30% by volume of the composition as prepared above, was added to the composition prior to its application to the surface of the soil. Preferably, the amount of adjuvant added to the composition of invertebrate pest control agent is in the range of about 0.01% to about 5% by volume, and more preferably, in the range of 0.08% to about 3% by volume.

A particularly preferred composition of the present invention is that where the invertebrate pest control agent in the liquid invertebrate pest control agent is bifenthrin, and the adjuvant added to the liquid invertebrate pest control agent is at least one adjuvant selected from i), ii), and xi), or mixtures thereof, where the concentration of the adjuvant is in the range of about 0.08% to about 3% by volume of the composition. In a particularly preferred composition, adjuvant (i) is most preferred.

The following examples further illustrate the present invention, but, of course, should not be construed as in any way limiting its scope. The examples set forth certain biological data illustrating the efficacy of the compositions of the present invention in enhancing the downward and lateral movement of an invertebrate pest control agent when applied to soil when compared to the same downward and lateral movement of an invertebrate pest control agent without the adjuvants of the present invention. Unless otherwise indicated, all parts, percentages, and the like are by weight.

EXAMPLE 1

Test to Determine Downward Movement of Bifenthrin Plus Adjuvant

The compositions of the present invention were tested for soil mobility by assessing the depth of penetration into soil of the invertebrate pest control agent contained therein by first placing the compositions of the present invention onto the top of columns of soil, followed by introduction of termites to the bottom of the columns of soil, then measuring the length of termite tunneling up into the soil. The depth of penetration into soil of the invertebrate pest control agent is therefore inversely proportional to the length of termite tunneling up into the soil. Specifically, the tests were conducted as follows:

Liquid invertebrate pest control agents in combination with certain adjuvants were tested for enhanced movement in soil of the invertebrate pest control agent contained therein, as compared to the movement in the soil of the invertebrate pest control agent alone without the adjuvant. These tests were conducted using a method adapted from Su et al, J. Econ. Entomology, 88: 1690-1694 (1995), as follows:

A test composition made up of TALSTAR® TERMITICIDE/INSECTICIDE in distilled water was prepared that provided a 0.06% (wt/v) suspension of bifenthrin. Measured aliquots of the bifenthrin suspension were then mixed with the requisite amount of a test adjuvant to provide 0.1% and 0.5% (v/v) solutions of the adjuvant.

Glass tubing, 13 mm in diameter, was then cut into 20 cm sections in sufficient quantity to conduct the test. Each 20 mm section of tubing was marked at 5 cm, 8 cm, and 18 cm distances from one end of the tube designated as the bottom. Each section of tubing was packed with a sandy soil (3% wt/wt moisture content) by first placing a section of a 1 cm diameter wooden dowel into the bottom of the glass tube up to the 8 cm marking, then introducing approximately 2 cm of soil into the other end of the tube designated as the top. The soil was then gently packed into the tube from the top using a second section of the 1 cm diameter wooden dowel. The process was repeated using 2 cm aliquots of soil until the soil level was adjacent to the 18 cm marking, thereby providing a column of soil 10 cm in height. An agar plug, which was formed in a section of the 13 mm diameter glass tubing of the type used to conduct these tests, was cut into 3 cm sections. A 3 cm section of agar was then gently pushed into the bottom of each tube containing the soil until the agar plug firmly touched the soil at the 8 cm marking, thereby creating a 5 cm void in the bottom of each section of tubing. Following placement of the agar plugs in each section of tubing; two sections of applicator sticks cut in 6 cm lengths were inserted into the bottom end of each tube thereby forcing about 1 cm of each stick into the agar plug to hold the agar plug in place. Plastic caps, with an inside diameter of 13 mm and holes drilled in their centers, were placed on the bottom ends of each of the sections of tubing. A sharpened applicator stick was then inserted into the hole in each plastic cap through the agar plug to the intersection of the agar plug and the soil. The applicator stick was then gently removed in a rotating manner to provide a means for a free flow of liquid through the soil. Each section of tubing was then stood upright, and 0.5 mL aliquots of each suspension of bifenthrin containing 0.1% and 0.5% of the test adjuvant, as prepared above, were pipetted onto the top of the soil. At least four replicates for each concentration of adjuvant were provided. In addition, there was also provided a similar number of replicates of a 0.6% suspension of bifenthrin alone, and also untreated controls. Upon application of the test suspensions of bifenthrin and test adjuvants, the top of each section of tubing was covered with a small piece of aluminum foil. The tubes were then allowed to stand for about 20 hours to allow movement of the bifenthrin and test adjuvant downward into the soil. After this time a plastic cap of 13 mm inside diameter was placed on the top of each section of tubing. The plastic caps with the holes drilled in their centers were removed from the bottom of each section of tubing, and a piece of 0.5 cm×4 cm filter paper was then placed between the two sections of applicator sticks. Fifty termite (*Reticulitermes flavipes*) workers were then inserted into the 5 cm void in the bottom of each section of tubing. New plastic caps without holes drilled in their centers were placed on the bottom of each section of tubing. The sections of tubing were then stored in an upright position, with the termites located below the soil. At 7 and 21 days post-infestation, termite mortality and distance of termite tunneling up into the soil was measured. The measurements were used to calculate a percent reduction of termite tunneling in the sections of tubing containing bifenthrin and test adjuvant as compared to termite tunneling in sections of tubing containing bifenthrin alone. The following results were recorded:

TABLE 1

Soil Movement of Bifenthrin Plus Adjuvant as Compared to Bifenthrin Alone Measured By Percent Reduction in Termite Tunneling

| | | 7 Days | | | 21 Days | | |
|---|---|---|---|---|---|---|---|
| Adjuvant Added | Rate of Appln. Adjuvant (% v/v) | Tunneling (cm) | Percent Red'n of Tunneling | Percent Mortality | Tunneling (cm) | Percent Red'n of Tunneling | Percent Morality |
| None | 0 | 7.2 | — | 0 | 7.4 | — | 0 |
| (i) | 0.1 | 4.3 | 40.3 | 0 | 4.4 | 40.5 | 0 |
| | 0.5 | 3.8 | 47.2 | 75 | 3.8 | 48.6 | 75 |

TABLE 1-continued Soil Movement of Bifenthrin Plus Adjuvant as Compared to Bifenthrin Alone Measured By Percent Reduction in Termite Tunneling

| Adjuvant Added | Rate of Appln. Adjuvant (% v/v) | 7 Days | | | 21 Days | | |
| --- | --- | --- | --- | --- | --- | --- | --- |
| | | Tunneling (cm) | Percent Red'n of Tunneling | Percent Mortality | Tunneling (cm) | Percent Red'n of Tunneling | Percent Morality |
| None | 0 | 7.1 | — | 17 | 7.2 | — | 28 |
| (i) | 0.1 | 5.4 | 23.9 | | 5.5 | 23.6 | 38 |
| 2nd Test | 0.5 | 2.7 | 62.0 | 68 | 2.7 | 63.5 | 71 |
| None | 0 | 7.0 | — | 25 | 7.0 | — | 50 |
| (ii) | 0.1 | 5.0 | 28.6 | 25 | 6.6 | 5.7 | 25 |
| | 0.5 | 3.8 | 45.7 | 66 | 3.8 | 45.7 | 100 |
| None | 0 | 7.3 | — | 25 | 7.3 | — | 25 |
| (ii) | 0.1 | 7.0 | 4.1 | 25 | 7.1 | 2.7 | 65 |
| 2nd Test | 0.5 | 6.1 | 16.4 | 0 | 6.1 | 16.4 | 100 |
| None | 0 | 7.4 | — | 0 | 7.5 | — | 25 |
| (ii) | 0.1 | 6.1 | 17.6 | 75 | 6.2 | 17.3 | 75 |
| 3rd Test | 0.5 | 5.1 | 32.4 | 1 | 5.1 | 32.0 | 50 |
| None | 0 | 6.8 | — | 0 | 6.9 | — | 0 |
| (ii) | 0.1 | 6.6 | 5.9 | 0 | 6.7 | 2.9 | 100 |
| 4th Test | 0.5 | 2.6 | 61.8 | 0 | 2.7 | 60.9 | 100 |
| None | 0 | 5.9 | — | 33 | 6.4 | — | 51 |
| (ii) | 0.1 | 3.9 | 33.9 | 36 | 4.9 | 23.4 | 37 |
| 5th Test | 0.5 | 2.0 | 66.1 | 42 | 2.9 | 54.7 | 92 |
| None | 0 | 7.6 | — | 52 | 7.6 | — | 100 |
| (iii) | 0.1 | 7.2 | 5.3 | 75 | 7.2 | 5.3 | 100 |
| | 0.5 | 6.0 | 21.1 | 26 | 6.1 | 19.7 | 75 |
| None | 0 | 7.3 | — | 25 | 7.3 | — | 25 |
| (iii) 2nd Test | 0.1 | 6.2 | 15.1 | 52 | 6.2 | 15.1 | 74 |
| None | 0 | 6.6 | — | 26 | 6.6* | — | 51 |
| (iii) | 0.1 | 6.4 | 3.0 | 0 | 6.5* | 1.5 | 25 |
| 3rd Test | 0.5 | 5.8 | 12.1 | 28 | 5.9* | 10.6 | 50 |
| None | 0 | 7.2 | — | 0 | 7.4 | — | 0 |
| (iii) 4th Test | 0.1 | 6.1 | 15.3 | 28 | 6.3 | 14.9 | 50 |
| None | 0 | 6.9 | — | 17 | 6.9 | — | 18 |
| (iii) | 0.1 | 6.2 | 10.1 | 0 | 6.3 | 8.7 | 0 |
| 5th Test | 0.25 | 6.2 | 10.1 | 42 | 6.2 | 10.1 | 50 |
| None | 0 | 7.0 | — | 25 | 7.0 | — | 50 |
| (iv) | 0.1 | 4.8 | 31.4 | 25 | 5.0 | 28.6 | 25 |
| | 0.5 | 3.6 | 48.6 | 0 | 3.6 | 48.6 | 0 |
| None | 0 | 7.6 | — | 52 | 7.6 | — | 100 |
| (v) | 0.1 | 5.0 | 34.2 | 75 | 5.0 | 34.2 | 100 |
| | 0.5 | 4.3 | 43.4 | 77 | 4.3 | 43.4 | 100 |
| None | 0 | 7.3 | — | 25 | 7.3 | — | 25 |
| (v) 2nd Test | 0.5 | 3.8 | 47.9 | 0 | 3.8 | 47.9 | 5 |
| None | 0 | 7.5 | — | 1 | 7.5 | — | 25 |
| (vi) | 0.1 | 3.6 | 52.0 | 25 | 3.7 | 50.7 | 25 |
| | 0.5 | 5.4 | 28.0 | 0 | 5.4 | 28.0 | 66 |
| None | 0 | 7.5 | — | 1 | 7.5 | — | 25 |
| (vii) | 0.1 | 5.5 | 26.7 | 25 | 5.5 | 26.7 | 25 |
| | 0.5 | 4.4 | 41.3 | 0 | 4.4 | 41.3 | 26 |
| None | 0 | 7.5 | — | 1 | 7.5 | — | 25 |
| (viii) | 0.1 | 5.2 | 30.7 | 0 | 5.5 | 26.7 | 25 |
| | 0.5 | 4.2 | 44.0 | 0 | 4.2 | 44.0 | 0 |
| None | 0 | 7.2 | — | 0 | 7.4 | — | 0 |
| (ix) | 0.1 | 6.7 | 6.9 | 25 | 6.8 | 8.1 | 50 |
| | 0.5 | 4.3 | 40.3 | 50 | 4.3 | 41.9 | 75 |
| None | 0 | 7.2 | — | 0 | 7.4 | — | 0 |
| (x) | 0.1 | 4.4 | 38.9 | 25 | 4.4 | 40.5 | 76 |
| | 0.5 | 3.4 | 52.8 | 0 | 3.5 | 52.7 | 70 |
| None | 0 | 6.2 | — | 25 | 6.7 | — | 50 |
| (xi) | 0.1 | 4.2 | 32.3 | 0 | 4.4 | 34.3 | 33 |
| | 0.5 | 1.6 | 74.2 | 0 | 2.8 | 58.2 | 25 |
| None | 0 | 6.2 | — | 25 | 6.7 | — | 50 |
| (xii) | 0.1 | 4.2 | 32.3 | 25 | 4.2 | 37.3 | 25 |
| | 0.5 | 3.4 | 45.2 | 75 | 3.4 | 49.3 | 75 |

*Results recorded at 22 days

A study of the table of data presented above indicates that all of the adjuvants in certain tests, except adjuvant (iii), reduced termite tunneling by at least 40%, which is indicative of the improved movement of the invertebrate pest control agent in soil. For example, tests conducted with adjuvants (i), (ii), (iv), (v), (vi), (x), (xi), and (xii) reduced termite tunneling by at least 48%, and tests conducted with adjuvants (i), (ii), and (xi) reduced termite tunneling by at least 58%.

EXAMPLE 2

Test to Determine Downward and Lateral Movement of Bifenthrin Plus Adjuvant

Downward and lateral movement in the soil of the invertebrate pest control agent bifenthrin was measured. These test were conducted using a 30.5 cm×30.5 cm wooden boxes. The boxes were made up of a series of stacked square wooden frames (30.5 cm×30.5 cm×1.9 cm), which could be stacked to any desired depth. These frames were stacked inside an outer support housing to maintain the box's structural integrity. It was determined that 10% soil moisture was an ideal range to evaluate the movement of soil applied invertebrate pest control agent for the Princeton 50/50 (sand:soil) soil. The soil moisture was altered by adding the appropriate amount of water to air-dried soil in a mixer (a rotating 5 gallon container) and mixing it until the soil was uniformly moist. The soil was then removed from the mixer and placed into a sealed bucket until enough soil was collected to fill a box. The moistened soil was added to the box in small amounts (~500 mL each scoop) and packed down using a wooden block (30.5 cm×30.5 cm×2.5 cm) and a rubber mallet. Once enough soil was added to fill the box to the desired depth, the center of the box is determined and a 5 cm circle was marked in the soil. The treatments were then applied to the soil by dripping the solutions from separatory funnels onto the 5 cm circle in the center of each box. The flow was adjusted so that each solution was applied without allowing it to spill out of the 5 cm treatment area.

The soil was treated with one of four treatments. The first was a liquid invertebrate pest control agent containing TALSTAR® GC FLOWABLE INSECTICIDE/MITICIDE alone, at a rate equivalent to the field rate (4 gallons of a 0.06% active ingredient of bifenthrin suspension per 10 linear feet). The second was the above-mentioned liquid invertebrate pest control agent plus adjuvant (i), at a rate of 0.5% (v/v). The third was the above-mentioned liquid invertebrate pest control agent plus adjuvant (ii), described below, at a rate of 0.5% (v/v), and the fourth was the above-mentioned liquid invertebrate pest control agent plus adjuvant (iii), described below, at a rate of 0.5% (v/v).

Once the treatments were applied, the boxes were covered with plastic bags to prevent moisture loss. The treated soils remained undisturbed for 24 hours to allow for maximum bifenthrin movement before they were cross-sectioned and infested with termites.

After 24 hours, the treated soils were then cross-sectioned by placing a wooden block (30.5 cm×30.5 cm×2.5 cm) on the soil surface and applying pressure to the block while pushing metal sheets between the wooden frames and slicing through the soil. This provided cross-sections that were 1.9 cm in depth and 30.5 cm×30.5 cm square. The soil cross-sections were then removed from the boxes, one at a time, and a plastic grid was placed upon the soil surface of each cross-section and lightly tapped into place. This procedure was repeated until all of the desired cross-sections were removed.

The center of each grid was then marked and the grids were then removed from the soil surface. Soil samples were then taken from each cross-section in a "+" pattern so that bifenthrin movement could be measured in all four directions, i.e., laterally from the point of application of bifenthrin.

Soil samples (ca. 3.2 cm×3.2 cm) were carefully removed and placed into individually labeled petri dishes (50×9 mm). Five worker termites (*Coptotermes formosanus*) were then added to each petri dish. The dishes were placed in an environmentally controlled chamber at 25° C. for 24 hours. Mortality was then recorded for each dish so that a three dimensional picture of bifenthrin soil movement could be constructed based upon the termite mortality in the soil sub-samples. The following results were recorded:

TABLE 2

Soil Movement of The Termiticide Bifenthrin Plus Adjuvant as Compared to Bifenthrin Alone Measured By Termite Mortality

| | Lateral Distance (cm) From Point of Application In Which Termite Percent Mortality Counts Were Taken | | | | |
|---|---|---|---|---|---|
| | 0-5.1 | 5.1-10.2 | 10.2-15.2 | 15.2-20.3 | 20.3-25.4 |
| Adjuvant Added: (i)[1] Depth of Soil (cm) | | | | | |
| 0-1.9 | 100% | 100 | 100 | 100 | 35 |
| 1.9-3.8 | 100 | 100 | 100 | 100 | 0 |
| 3.8-5.7 | 100 | 100 | 100 | 75 | 0 |
| 5.7-7.6 | 100 | 100 | 100 | 80 | 0 |
| 7.6-9.5 | 100 | 100 | 100 | 20 | 0 |
| 9.5-11.4 | 100 | 75 | 0 | 0 | 0 |
| 11.4-13.3 | 100 | 5 | 0 | 0 | 0 |
| 13.3-15.2 | 0 | 0 | 0 | 0 | 0 |
| Adjuvant Added: (ii)[1] Depth of Soil (cm) | | | | | |
| 0-1.9 | 100% | 100 | 100 | 30 | 45 |
| 1.9-3.8 | 100 | 100 | 100 | 10 | 0 |
| 3.8-5.7 | 100 | 100 | 100 | 20 | 20 |
| 5.7-7.6 | 100 | 100 | 100 | 5 | 15 |
| 7.6-9.5 | 100 | 100 | 100 | 5 | 15 |
| 9.5-11.4 | 100 | 100 | 25 | 5 | 5 |
| 11.4-13.3 | 100 | 55 | 0 | 0 | 0 |
| 13.3-15.2 | 0 | 0 | 0 | 0 | 0 |
| Adjuvant Added: (iii)[1] Depth of Soil (cm) | | | | | |
| 0-1.9 | 100% | 100 | 100 | 50 | 50 |
| 1.9-3.8 | 100 | 100 | 100 | 5 | 0 |
| 3.8-5.7 | 100 | 100 | 70 | 0 | 0 |
| 5.7-7.6 | 100 | 100 | 65 | 5 | 0 |
| 7.6-9.5 | 90 | 45 | 5 | 0 | 0 |
| 9.5-11.4 | 5 | 0 | 0 | 0 | 0 |
| 11.4-13.3 | 0 | 0 | 0 | 0 | 0 |
| Adjuvant Added: None (Bifenthrin Alone) Death of Soil (cm) | | | | | |
| 0-1.9 | 100% | 100 | 65 | 25 | 25 |
| 1.9-3.8 | 100 | 100 | 100 | 10 | 0 |

TABLE 2-continued

Soil Movement of The Termiticide Bifenthrin Plus Adjuvant as Compared to Bifenthrin Alone Measured By Termite Mortality

| | Lateral Distance (cm) From Point of Application In Which Termite Percent Mortality Counts Were Taken | | | | |
|---|---|---|---|---|---|
| | 0-5.1 | 5.1-10.2 | 10.2-15.2 | 15.2-20.3 | 20.3-25.4 |
| 3.8-5.7 | 100 | 100 | 25 | 0 | 0 |
| 5.7-7.6 | 100 | 50 | 0 | 0 | 0 |
| 7.6-9.5 | 30 | 0 | 0 | 0 | 0 |
| 9.5-11.4 | 0 | 0 | 0 | 0 | 0 |

The formulation used in these experiments to prepare the liquid invertebrate pest control agent is sold under the name and trademark of Talstar GC FLOWABLE INSECTICIDE/MITICIDE. The invertebrate pest control agent in the formulation is bifenthrin. In each experiment the liquid invertebrate pest control agent was applied at a rate equivalent to 4 gallons of 0.06% a.i. bifenthrin/10 linear feet.
[1]The concentration of the adjuvant was 0.5% (V/V) of the amount of liquid invertebrate pest control agent applied.

As set forth in Table 2 above, without addition of any adjuvant of the present invention to the liquid invertebrate pest control agent containing the Talstar GC Flowable formulation of the invertebrate pest control agent bifenthrin, the bifenthrin moved across the soil surface (laterally) a total lateral diameter of 16.5 cm from the 5 cm treatment area. The bifenthrin moved downwardly to a depth of 7.6-10.2 cm and a diameter of 10.2 cm at the point of deepest penetration.

The addition of adjuvant (i) to the liquid invertebrate pest control agent containing the Talstar GC Flowable formulation increased the overall (downward and lateral) movement of bifenthrin by 30-40%. By adding adjuvant (i), the total lateral surface diameter increased from 15.2 cm to 25.4 cm and the depth of penetration increased from 7.6-10.2 cm to 11.4-14.0 cm and a diameter of 10.2 cm at the point of deepest penetration.

The addition of adjuvant (ii) to the liquid invertebrate pest control agent containing the Talstar GC Flowable formulation increased the overall movement of bifenthrin by 20-30%. By adding adjuvant (ii), the total lateral surface diameter increased from 15.2 cm to 24.1 cm and the depth of penetration increased from 7.6-10.2 cm to 10.2-12.7 cm and a diameter of 10.2 cm at the point of deepest penetration.

The addition of adjuvant (iii) to the liquid invertebrate pest control agent containing the Talstar GC Flowable formulation increased the overall movement of bifenthrin by 20-25%. The addition of adjuvant (iii) increased the total lateral surface diameter from 15.2 cm to 24.1 cm, but the depth of penetration remained the same as bifenthrin alone.

The modifier "about" is used herein to indicate that certain preferred operating ranges, such as ranges for material amounts, temperature, and the like are not fixedly determined. The meaning will often be apparent to one of ordinary skill. For example, a recitation of a concentration of about 0.1% to about 5% in reference to, for example, a soil-borne invertebrate pesticidal composition would be interpreted to include other like concentrations that can be expected to favor soil-borne invertebrate pest control, such as 0.09% or 5.5%. Where guidance from the experience of those of ordinary skill is lacking, guidance from the context is lacking, and where a more specific rule is not recited presented below, the "about" range shall be not more than 10% of the absolute value of an end point or 10% of the range recited, whichever is less. In the context of the present invention, the term "soil-borne invertebrate pest control agent", or "invertebrate pest control agent" refers to a "termiticide", or to an "insecticide" useful for control of soil-borne insects other than termites, or to a "nematicide"; or to a "termiticide/insecticide/nematicide"; which in turn refers to the active chemical compound or ingredient, such as bifenthrin, that kills or repels termites, soil-borne insects other than termites, and nematodes. The term "liquid invertebrate pest control agent" or "liquid soil-borne invertebrate pest control agent" refers to a composition comprised of a formulation of an invertebrate pest control agent where the formulation can be dispensed in an aqueous medium prior to its application to a locus where invertebrate pest control is desired. The term "adjuvant" refers to any emulsifier, surfactant, wetting agent, solvent, diluent, penetrant, or the like, which, when added to invertebrate pest control agents, or to liquid invertebrate pest control agents comprised of formulations of invertebrate pest control agents, promotes movement of the invertebrate pest control agent in soil. The term "repellency" refers to driving back, warding off, or keeping soil-borne invertebrate pests away through the use of an invertebrate pest control agent to provide a suitable pest-controlling barrier. The terms "mortality", "percent mortality", "control", or "percent control" may be used interchangeably, and refer to the killing of and/or repelling of soil-borne invertebrate pests.

Those of ordinary skill in the art will appreciate that variations of the invention may be used and that it is intended that the invention may be practiced otherwise than as specifically described herein. Accordingly, this invention includes all modifications encompassed within the spirit and scope of the invention as defined by the following claims.

What is claimed is:

1. A method for the control of soil-borne invertebrate pests, comprising applying to soil, a pesticidally effective amount of a composition comprised of:
    a solid soil-borne invertebrate pest control agent selected from the group consisting of bifenthrin, isomers of bifenthrin, and mixtures thereof, and
    B) an emulsifier of 99% 2,4,6-tris[1-(phenyl)ethyl]phenyl-omega-hydroxy-poly(oxyethylene)sulphate,
        wherein said emulsifier promotes at least a 20% increase in downward and lateral movement of said invertebrate pest control agent in soil relative to the downward and lateral movement of said invertebrate pest control agent in soil without said emulsifier.

2. The method of claim 1 wherein said emulsifier promotes said increase in downward and lateral movement of said soil-borne invertebrate pest control agent in soil by at least 30%.

3. The method of claim 1, wherein the composition includes about 0.001% to about 30% by volume of said emulsifier.

4. The method of claim 3, wherein the composition includes about 0.01% to about 5% of said emulsifier.

5. The method of claim 4, wherein the composition includes about 0.08% to about 3% of said emulsifier.

6. The method of claim 1, wherein said soil-borne invertebrate pest control agent is bifenthrin, and the concentration of the emulsifier is about 0.08% to about 3% by volume.

7. The method of claim 1, wherein said soil-borne invertebrate pests are termites, nematodes, corn rootworms or wireworms.

8. The method of claim 6, wherein said soil-borne invertebrate pests are termites, nematodes, corn rootworm or wireworms.

9. The method of claim 7, wherein said soil-borne invertebrate pests are termites, wherein termite tunneling in soil is reduced by at least 40%.

10. The method of claim 8, wherein said soil-borne invertebrate pests are termites, wherein termite tunneling in soil is reduced by at least 48%.

11. The method of claim 6, wherein said soil-borne invertebrate pests are termites, wherein termite tunneling in soil is reduced by at least 58%.

* * * * *